(12) United States Patent
Mullet et al.

(10) Patent No.: US 8,597,254 B1
(45) Date of Patent: Dec. 3, 2013

(54) MEDICAL LINE SECUREMENT SYSTEM

(75) Inventors: Joyce Mullet, Columbus, OH (US); Nancy Ryan-Wenger, Canal Winchester, OH (US); Micah Skeens, Gahanna, OH (US)

(73) Assignee: Nationwide Children's Hospital, Inc., Columbus, OH (US)

( * ) Notice: Subject to any disclaimer, the term of this patent is extended or adjusted under 35 U.S.C. 154(b) by 40 days.

(21) Appl. No.: 12/878,734

(22) Filed: Sep. 9, 2010

Related U.S. Application Data

(60) Provisional application No. 61/240,853, filed on Sep. 9, 2009.

(51) Int. Cl.
*A61M 5/32* (2006.01)
*A61M 5/00* (2006.01)
*A61M 5/178* (2006.01)

(52) U.S. Cl.
USPC ........... 604/174; 604/177; 604/179; 604/263; 604/164.08

(58) Field of Classification Search
USPC ............ 128/DIG. 6, 26, 15; 604/103, 164.08, 604/164.04, 241–243, 263
See application file for complete search history.

(56) References Cited

U.S. PATENT DOCUMENTS

| | | | | |
|---|---|---|---|---|
| 3,561,442 A | * | 2/1971 | Goswitz | 602/41 |
| 4,862,904 A | * | 9/1989 | West et al. | 128/877 |
| 5,417,668 A | * | 5/1995 | Setzer et al. | 604/263 |
| 5,897,519 A | * | 4/1999 | Shesol et al. | 602/79 |
| 6,311,933 B1 | * | 11/2001 | Starchevich | 248/65 |
| 6,749,601 B2 | * | 6/2004 | Chin | 606/1 |
| 7,077,142 B1 | * | 7/2006 | Barany et al. | 128/877 |
| 2008/0132821 A1 | * | 6/2008 | Propp et al. | 602/54 |

FOREIGN PATENT DOCUMENTS

WO    WO 2008151047 A1 * 12/2008

* cited by examiner

*Primary Examiner* — Bhisma Mehta
*Assistant Examiner* — Lauren M Peng
(74) *Attorney, Agent, or Firm* — Roger A. Gilcrest

(57) ABSTRACT

The present invention is a protective sleeve for containing medical lines, comprising: (a) a foldable sleeve comprising first and second side panels, and adapted to be opened and closed along its longitudinal axis so as to form a conduit for medical lines, at least one of the panels being transparent, the foldable sleeve adapted to be reversibly opened along its longitudinal axis, and having releasable closures to maintain the foldable sleeve in a folded closed position; and (b) a plurality of rigid members incorporated into the sleeve and along the longitudinal axis.

22 Claims, 12 Drawing Sheets

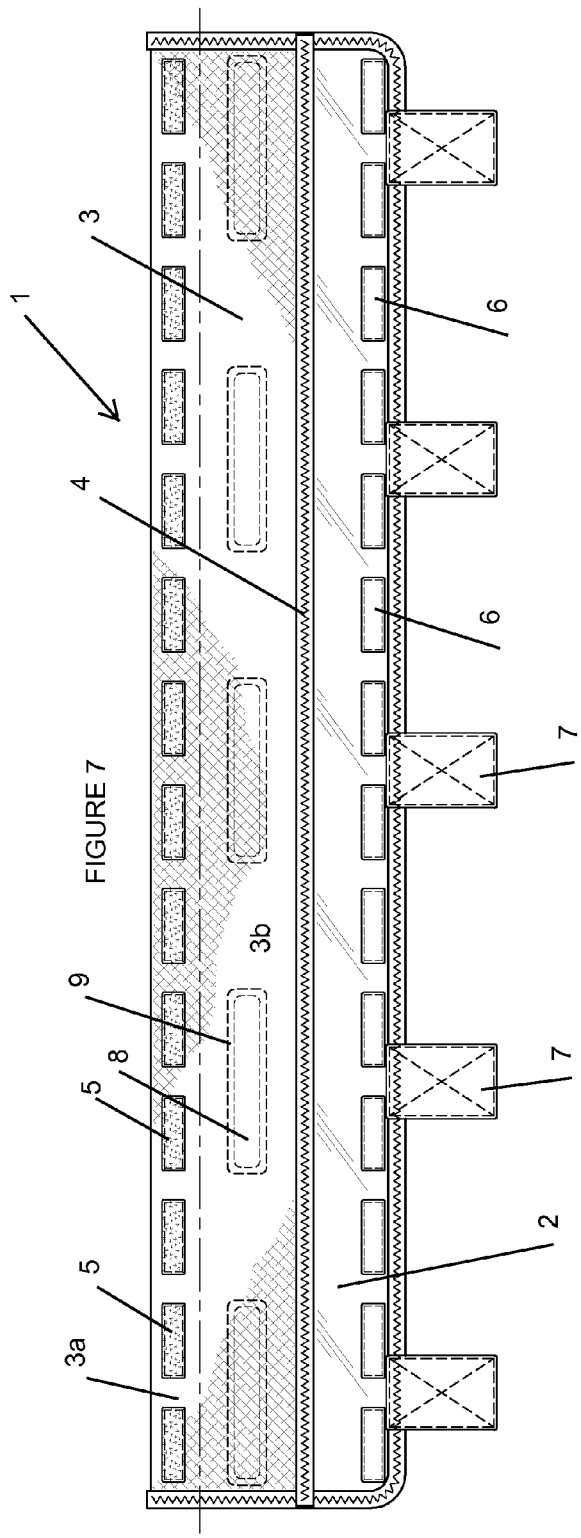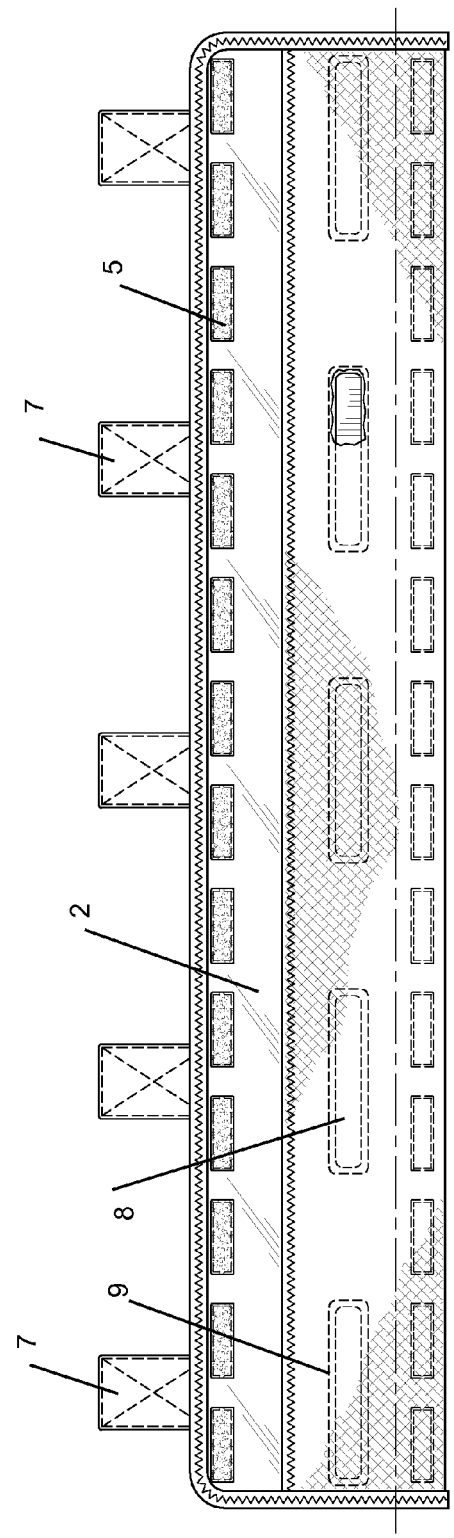

MEDICAL LINE SECUREMENT SYSTEM

RELATED APPLICATION DATA

This application claims the priority benefit of U.S. Provisional Application Ser. No. 61/240,853, filed Sep. 9, 2009, which is hereby incorporated in its entirety herein by reference.

BACKGROUND

Medical lines of various types are typically present in the clinical setting in connection with institutional and at-home care for patients. Medical lines can include intravenous lines used for the delivery of fluids, blood, and therapeutic and prophylactic agents, device monitoring lines, feeding tubes, and tubes for delivery of gas, such as oxygen. Such lines are affixed to the patient at a first end and to a medical device, such as an infusion pump, monitor, or valve at a second end. The length of the line is typically sufficient to allow for some range of movement of the patient away from the medical device, and most medical lines are flexible. Thus, such lines commonly become intertwined, leading to the risks of confusion and damage to the lines or to the patient or equipment. Further, such lines are likely to be contaminated by contact with the floor, the patient bed, persons in the patient room, and devices near the patient, thus increasing the risk of the entry into the patient of pathogens. Moreover, in many instances, such medical lines are prone to entanglement with the patient. In most circumstances, the harm associated with such entanglement is kinking or breakage of the medical line, or disengagement from the patient or the medical device, or some other form of damage to medical equipment. In some more unfortunate circumstances, entanglement with the patient can lead to patient injury or death by asphyxiation. This is a more significant concern with pediatric patients and with disabled or unconscious patients. Thus, there is a need for devices and methods for securing medical lines so as to minimize the risk of dangerous entanglement with patients, and to minimize the likelihood of confusion between medical lines and line contamination.

BRIEF SUMMARY

Provided in various embodiments are securement systems and devices useful for prevention of patient entanglement and possible strangulation with medical lines. Such systems and devices are also useful for minimization of pathogenic contamination of, and cross contamination between intravenous, feeding and other lines, and these systems and devices are useful for organization and discrete identification of medical lines.

In general terms, the invention may be described as a protective sleeve for containing medical lines, the sleeve comprising: (a) a foldable sleeve comprising first and second side panels, and adapted to be opened and closed along its longitudinal axis so as to form a conduit for medical lines, at least one of the panels being transparent, the foldable sleeve adapted to be reversibly opened along its longitudinal axis, and having releasable closures to maintain the foldable sleeve in a folded closed position; and optionally (b) a plurality of rigid members incorporated into the sleeve and along the longitudinal axis.

The releasable closures may be an effective closure for releasable/reversible closing of the sleeve, such as those selected from the group consisting of Velcro, magnets, hooks, buckles, buttons, zippers and snaps. It is preferred that the releasable closures comprise a series of Velcro closures disposed along a length of the protective sleeve so as to permit partial opening of the protective sleeve.

The plurality of rigid members preferably are enclosed within one of the panels. It is also preferred that the plurality of rigid members are substantially the same length, and disposed in a series with flexible portions of the panels disposed therebetween, so as to permit the protective sleeve to be folded in a series of lengths approximating the length of the rigid members.

In a preferred embodiment, the protective sleeve may additionally comprise an attachment means for attaching the protective sleeve to a stationary object, such as a wall, a patient's chair or bed, a medical instrument, or a support structure, such as an I.V. pole or the like. Such means may be a series of hooks, material tabs, Velcro loops or mechanical hand clamps or adhesive strips, or a series of tabs, disposed along a length of the protective sleeve and extending therefrom.

It is also preferred that the sleeve is made of a separable material, such as by containing a series of transverse perforations so as to be divisible into more than one portion. This optional feature is best applied when the protective sleeve is made of a readily separable material or material that can be rendered separable through perforation, such that the protective sleeve may be provided in a relatively substantial length, such as in a package or on a roll, allowing the user to size the sleeve to the desired application for medical lines of varying length.

The present invention also includes a protective sleeve as described herein wherein the sleeve contains at least one medical line, such as those selected from the group consisting of intravenous lines used for the delivery of fluids, blood, and therapeutic and prophylactic agents, device monitoring lines, feeding tubes, and tubes for delivery of gas.

In a more preferred embodiment, the protective sleeve for containing medical lines, comprises: (a) a foldable sleeve comprising first and second side panels, and adapted to be opened and closed along its longitudinal axis so as to form a conduit for medical lines, the first panel being transparent and the second panel being opaque, the foldable sleeve adapted to be reversibly opened along its longitudinal axis, and having releasable closures to maintain the foldable sleeve in a folded closed position, the releasable closures comprising a series of Velcro closures disposed along a length of the protective sleeve so as to permit partial opening of the protective sleeve; (b) a plurality of rigid members incorporated into the second panel and along the longitudinal axis; and (c) attachment means for attaching the protective sleeve to a stationary object. The attachment means may be any means for attaching the protective sleeve to a stationary object as described herein. The protective sleeve preferably contains a series of transverse perforations so as to be divisible into more than one portion.

In a most preferred embodiment, the protective sleeve comprises: (a) a foldable sleeve comprising first and second side panels, and adapted to be opened along its fold so as to form a conduit for medical lines, the first panel being transparent and the second panel being opaque, the foldable sleeve adapted to be reversibly opened along its longitudinal axis, and having releasable closures to maintain the foldable sleeve in a folded closed position, the releasable closures comprising a series of Velcro closures disposed along a length of the protective sleeve so as to permit partial opening of the protective sleeve; (b) a plurality of rigid members incorporated into the second panel and along the longitudinal axis, wherein the plurality of rigid members are substantially the same length, and disposed in a series with flexible portions of the panels disposed therebetween, so as to permit the protective sleeve to be folded in a series of lengths approximating the length of the rigid members; and (c) attachment means for attaching the protective sleeve to a stationary object.

Other features of the embodiments of the present invention will be apparent in light of the description of the invention embodied herein.

DESCRIPTION OF THE FIGURES

The following detailed description of specific embodiments of the present invention can be best understood when read in conjunction with the following figures in which:

FIG. 7 is a detailed plan view of the underside of a representative embodiment of the systems described herein, in accordance with one embodiment of the present invention, shown in a fully opened position;

FIG. 8 is a detailed plan view of the top side of a representative embodiment of the systems described herein, in accordance with one embodiment of the present invention, shown in a fully opened position, as shown in FIG. 1;

DETAILED DESCRIPTION

Figure 1:
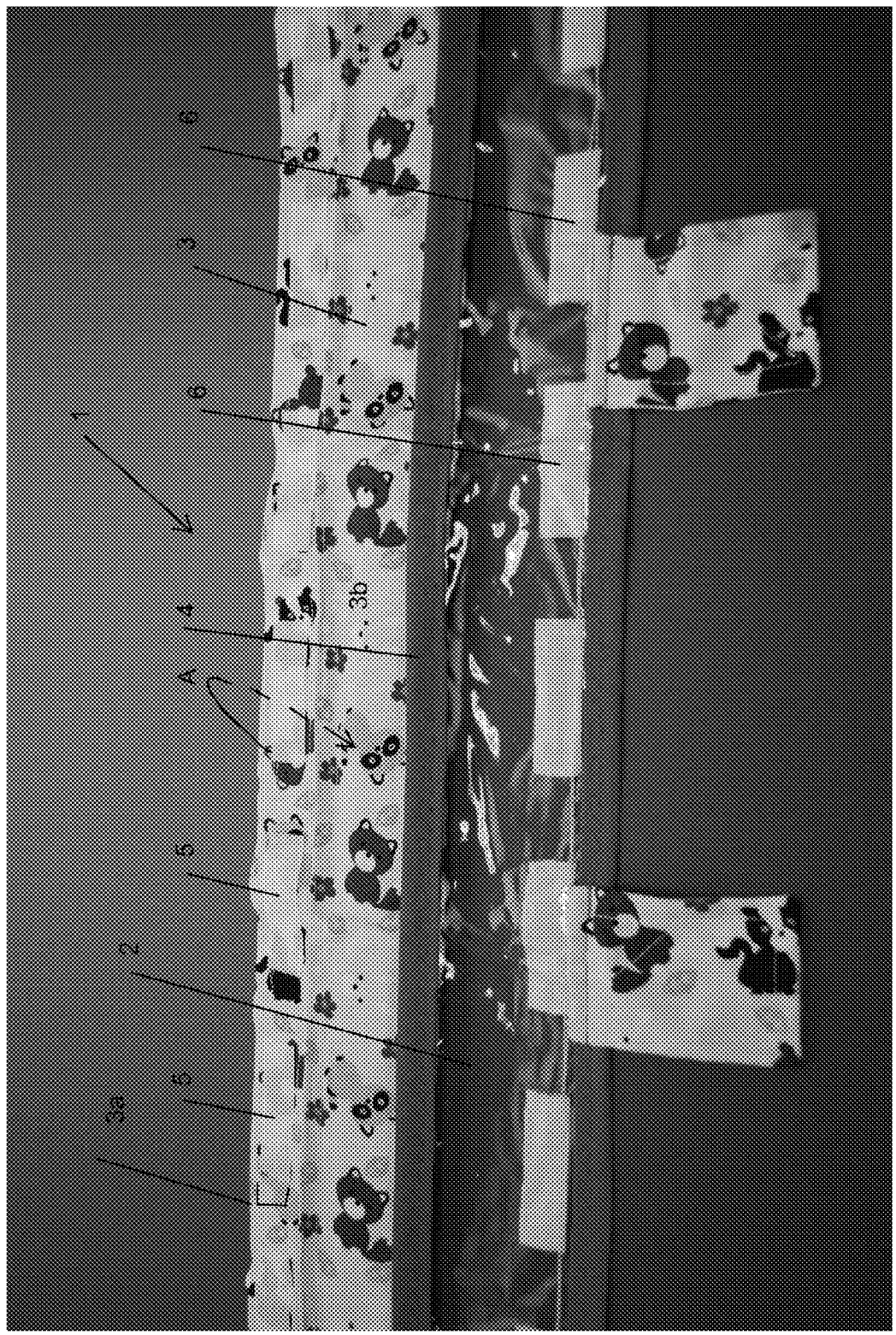
FIG. 1 is a partial detailed plan view of the underside of a representative embodiment of the systems described herein, in accordance with one embodiment of the present invention, shown in a fully opened position.

The following detailed description of various representative embodiments and the accompanying figures show by way of description and illustration, and not by way of limitation, representative embodiments. It is to be understood that other embodiments are contemplated though not depicted or described herein, and that logical, mechanical, chemical and electrical changes may be made without departing from the spirit and scope of the present invention.

The systems and devices herein are useful for, but not limited to: prevention of patient entanglement and possible strangulation with medical lines; minimization of pathogenic contamination of and cross contamination between intravenous, feeding and other medical lines that communicate with the blood or other internal organs or tissues of the patient; organization and discrete identification of medical lines to allow prompt access, adaptation, removal and adjustment of same; and combinations of these and potentially other uses.

In various embodiments, the systems include one or more protective sleeves. Each protective sleeve comprises an elongated pocket that encloses a portion of or substantially the entire length of a medical line. In some examples, medical lines, such as intravenous lines, have a standard length of approximately 36 inches. Thus, in some embodiments, the protective sleeve encloses a medical line from a point within inches of the patient, and up to a point close to the distal attachment of the medical line to a medical device (e.g., an intravenous bag that is attached to an intravenous line). In other embodiments, the protective sleeve encloses only a portion of a medical line, such that an intravenous line having a standard length of 36 inches may be enclosed within a protective sleeve that is from about 6 inches to about 30 inches in length. Thus, in various embodiments, depending on the length and type of medical line used with the devices and systems, the protective sleeve may have a length from about 6 inches to about 60 inches, and thus may be 6, 7, 8, 9, 10, 11, 12, 13, 14, 15, 16, 17, 18, 19, 20, 30, 40, 50, or 60 inches in length, and increments and fractional increments thereof and therebetween, from 0.1 to 0.9 fractional increments, thus including lengths having fractional increments of about 0.1, 0.2, 0.3, 0.4, 0.5, 0.6, 0.7, 0.8, and 0.9 inches. Of course, it will be appreciated by one of ordinary skill that variations of length that are less than six inches and greater than 30 inches are contemplated in the scope of the invention, and that under some circumstances, much shorter or much longer lengths outside of the range of typical lengths of medical lines are contemplated herein. As further described herein, the protective sleeves, closures, and fasteners may be formed together in a single piece or in multiple pieces, and may likewise individually be formed in a single or multiple piece, and from any of a variety of natural and synthetic materials, including but not limited to paper, cloth, metal, wood, plastic, and combinations of these. In typical embodiments, the protective sleeves and closures are flexible, such that they may be rolled or folded.

The systems can include closure devices that include fasteners and are used for attaching and fixing a protective sleeve to a medical line. The closures and fasteners may likewise be used to connect multiple protective sleeves to one another, or to connect one or more other divides or instruments to a protective sleeve, or combinations of these. The systems can also include one or a plurality of rigid elements that are combined with the protective sleeve for arrangement along all or a portion of the length of the medical line so as to prevent kinking of the line and wrapping or entanglement of the line with itself, with other lines and objects, and most particularly with the head or neck of the patient.

In some embodiments, then, the systems include elongated protective sleeves that have affixed to them several rigid elements and are adapted with one or more closures to attach to a medical line such that the line is prevented from wrapping around the neck of a patient. According to such embodiments, the protective sleeve is adapted to hold the rigid elements, each of which have a length from about 4 inches to about 10 inches, and in some particular embodiments have a length of about 6 inches, arrayed in series along the length of the protective sleeve and separated by about 1 inch to 3 inches. According to such embodiments, the protective sleeve is formed such that at least a portion of the protective sleeve is transparent, enabling the visualization of the enclosed medical line, and is closed by a means that prevents ready access to the line or removal of the sleeve by the patient. As such, closures that limit ready access to the line are provided and include one or more fasteners that are not easily actuated by the patient, particularly by a pediatric patient.

Thus, in various embodiments, depending on the length and type of medical line used with the devices and systems, one or more rigid elements may have a length from about 4 inches to about 10 inches, and thus may be 4, 5, 6, 7, 8, 9, or 10 inches in length, and increments and fractional increments thereof and therebetween, from 0.1 to 0.9 fractional increments, thus including lengths having fractional increments of about 0.1, 0.2, 0.3, 0.4, 0.5, 0.6, 0.7, 0.8, and 0.9 inches. Of course it will be appreciated by one of ordinary skill that variations of length that are somewhat less than four inches and somewhat greater than 10 inches are contemplated in the scope of the invention. Moreover, in various embodiments, depending on the length and type of medical line used with the devices and systems and the length of the rigid element, the spacing between two or more rigid elements may have a length from about 1 inches to about 3 inches, and thus may be 1, 2, or 3 inches in length, and increments and fractional increments thereof and therebetween, from 0.1 to 0.9 fractional increments, thus including lengths having fractional increments of about 0.1, 0.2, 0.3, 0.4, 0.5, 0.6, 0.7, 0.8, and 0.9 inches. Of course it will be appreciated by one of ordinary skill that variations of length that are somewhat less than 1 inch and somewhat greater than 3 inches are contemplated in the scope of the invention. As further described herein, the rigid elements may be formed in a single piece or in multiple pieces, and from any of a variety of natural and synthetic materials, including paper, metal, wood, cloth and plastic, and combinations of these.

Accordingly, the systems include various embodiments that comprise an elongated sleeve having a clear front panel and a color or pattern coated back panel that is keyed to a single medical line to be contained in the protective sleeve, and a series of inert plastic rigid members retained in pockets along the length of the protective sleeve, and one or a series of closures that close the sleeve along substantially its full length so as to protect the medical line from contact with objects outside of the protective sleeve, and one or a series of adaptations along the length of the line to permit access to the line while substantially maintaining the line within the protective sleeve, wherein the protective sleeve, the rigid members, and the closures are resistant to pathogens. It will be appreciated that other embodiments, as further described herein, are possible, such that systems comprising one or more of the component devices described herein may be provided, and having a variety of different configurations, lengths, and properties.

In various embodiments, the systems comprise one or more device components.

In some representative and non-limiting embodiments, the systems comprise a protective sleeve for enclosing all or a portion of one or more medical lines, the protective sleeve formed at least in part of a non-fabric, translucent or transparent material selected from polymers such as plastic, or plasticized materials having one or more of the properties of being wipable, sterilizable, non-porous, microbial resistant, antimicrobial, and comprising antimicrobial agents, the protective sleeve comprising spaced apart rigid elements formed of one or more materials selected from wood, metal, paper, plastic and combinations of these, and having one or more of the properties of being wipable, sterilizable, non-porous, microbial resistant, antimicrobial, and comprising antimicrobial agents, the protective sleeve comprising closures that allow easy attachment to a medical line and resist tampering by a patient, the closures comprising fasteners having one or more of the properties of being wipable, sterilizable, non-porous, microbial resistant or antimicrobial, and comprising antimicrobial agents and selected from magnets, zippers, and snaps that are compatible with imaging and radiographic equipment, the protective sleeve formed of or comprising a material that is coded based on color that conforms with a predetermined coding standard to enable ready identification of the line(s) enclosed therein.

The accompanying photographic figures show a representative but non-limiting embodiment that comprises a protective sleeve for enclosing all or a portion of one or more medical lines, the protective sleeve formed at least in part of a front panel formed of a non-fabric plastic that has the properties of being wipable, sterilizable, non-porous, and microbial resistant and a back panel formed of an aesthetically pleasing patterned fabric, the protective sleeve comprises spaced apart rigid elements formed of wood and inserted and concealed within pockets positioned along the length of the protective sleeve. The protective sleeve also comprises closures in the form of fabric tabs with fasteners that allow easy attachment to a medical line and resist tampering by a patient.

In other representative and non-limiting embodiments, the systems comprise a device having the features of a protective sleeve for housing one or more medical lines, the protective sleeve formed at least in part of a non-fabric, translucent or transparent material selected from polymers such as plastic, or plasticized materials having one or more of the properties of being wipable, sterilizable, non-porous, microbial resistant, anti-microbial, and comprising antimicrobial agents, the protective sleeve comprising spaced apart rigid elements formed of one or more materials, the protective sleeve comprising closures that allow attachment to a medical line and fasteners selected from Velcro, magnets, hooks, buckles, buttons, zippers, and snaps, the protective sleeve formed of or comprising a material that is coded based on color that conforms with a predetermined coding standard to enable ready identification of the line(s) enclosed therein.

In some embodiments, the systems comprise protective sleeves that enclose a portion or substantially all of at least one medical line. In some such embodiments, the protective sleeve is formed at least in part of a non-fabric, translucent or transparent material selected from polymers such as plastic, or plasticized materials. In some embodiments, the protective sleeve is formed at least in part of a material having one or more of the properties of being wipable, sterilizable, non-porous, microbial resistant, anti-microbial, and comprising antimicrobial agents. In some embodiments, the protective sleeve comprises front and back panels. In some such embodiments, the front and back panels are formed of the same material, and in other embodiments, the front and back panels are formed of different materials. In some embodiments, the systems comprise one or more closures that allow easy attachment of the protective sleeve to a medical line and resist tampering by a patient. In such embodiments, the one or more closures comprise one or more fasteners selected from magnets, zippers, buttons, hooks, Velcro, snaps and combinations of these. In some embodiments the one or more closures have one or more of the properties of being wipable, sterilizable, non-porous, microbial resistant or antimicrobial, and comprising antimicrobial agents. In some embodiments, the one or more closures are formed at least in part of a non-fabric, translucent or transparent material selected from polymers such as plastic or plasticized materials. The fasteners are, in some embodiments, formed of one or more materials that are generally compatible with imaging and radiographic equipment.

In some embodiments, the systems comprise protective sleeves that enclose a portion or substantially all of at least one medical line, and one or more rigid elements attachable to the protective sleeve for providing rigidity to prevent bending or kinking of the portion of the at least one medical line enclosed within the protective sleeve. In some such embodiments, the systems comprise a plurality of rigid elements for attachment to the protective sleeve in spaced-apart series for providing segments of rigidity along the at least one medical line to prevent bending or kinking of the portion of the at least one medical line enclosed within the protective sleeve.

In some embodiments, the systems comprise protective sleeves that enclose a portion or substantially all of at least one medical line, and one or more rigid elements attachable to the protective sleeve for providing rigidity to prevent bending or kinking of the portion of the at least one medical line enclosed within the protective sleeve, wherein the protective sleeve is formed at least in part of a non-fabric, translucent or transparent material selected from polymers such as plastic, or plasticized materials.

In some embodiments, the systems comprise protective sleeves that enclose a portion or substantially all of at least one medical line, and one or more rigid elements attachable to the protective sleeve for providing rigidity to prevent bending or kinking of the portion of the at least one medical line enclosed within the protective sleeve, wherein the protective sleeve is formed of a material having one or more of the properties of being wipable, sterilizable, non-porous, microbial resistant, antimicrobial, and comprising antimicrobial agents.

In some embodiments, the systems comprise protective sleeves that enclose a portion or substantially all of at least one medical line, and one or more rigid elements attachable to the protective sleeve for providing rigidity to prevent bending or kinking of the portion of the at least one medical line enclosed within the protective sleeve, wherein the protective sleeve comprises front and back panels. In some such embodiments, the front and back panels are formed of the same material, and in other embodiments, the front and back panels are formed of different materials. In some such embodiments, the protective sleeve comprises one or more additional panels for containing the one or more rigid elements.

In some embodiments, the systems comprise protective sleeves that enclose a portion or substantially all of at least one medical line, and one or more rigid elements attachable to the protective sleeve for providing rigidity to prevent bending or kinking of the portion of the at least one medical line enclosed within the protective sleeve, wherein the one or more rigid elements is formed of one or more materials having one or more of the properties of being wipable, sterilizable, non-porous, microbial resistant, antimicrobial, and comprising antimicrobial agents.

In some embodiments, the systems comprise protective sleeves that enclose a portion or substantially all of at least one medical line, and one or more rigid elements attachable to the protective sleeve for providing rigidity to prevent bending or kinking of the portion of the at least one medical line enclosed within the protective sleeve, and one or more closures that allow easy attachment to a medical line and resist tampering by a patient. In such embodiments, the one or more closures comprise one or more fasteners selected from magnets, zippers, buttons, hooks, Velcro, snaps and combinations of these. In some embodiments the one or more closures have one or more of the properties of being wipable, sterilizable, non-porous, microbial resistant or antimicrobial, and comprising antimicrobial agents. In some embodiments, the one or more closures are formed at least in part of a non-fabric, translucent or transparent material selected from polymers such as plastic, or plasticized materials. The fasteners are, in some embodiments, formed of one or more materials that are generally compatible with imaging and radiographic equipment.

In some embodiments, the systems comprise protective sleeves that enclose a portion or substantially all of at least one medical line, and one or more rigid elements attachable to the protective sleeve for providing rigidity to prevent bending or kinking of the portion of the at least one medical line enclosed within the protective sleeve, wherein the protective sleeve is adapted with discrete openings to allow ready access to a line port or other structure. In some such embodiments, the adaptations are openings designed to accommodate standard medical line configurations, such as the size and typical spacing of injection ports, and the like.

In some embodiments, the systems comprise protective sleeves that enclose a portion or substantially all of at least one medical line, and a means for coding the enclosed medical line or lines to enable ready identification and discrimination of each such line. In some embodiments, the means for identification and discrimination comprise color coding, or patterned coding, or textured coding, or auditory tagged coding or combinations of these. In some such embodiments, the means of coding is communicated on the sleeve as either a portion of the sleeve or an attachment thereto. Thus, in some embodiments, the protective sleeve may be formed of one or more panels, wherein at least one panel or a portion thereof comprises a coded material. In these various embodiments, the coding may be adapted to meet any known or standard coding conventions, such as those conventions associated with various types of medical lines, wherein oxygen gas lines are coded with a particular color, and intravenous lines are coded with a particular color and monitor lines are coded with a particular color and feeding lines are coded with a particular color, according to known or established conventions. Of course, it will be apparent to one of ordinary skill that any of a variety of conventional and non-conventional coding means may be employed for enabling the ready identification of and discrimination between multiple medical lines.

In some embodiments, the systems comprise an array of two or more protective sleeves each of which encloses a portion or substantially all of at least one medical line. According to some such embodiments, the protective sleeves are interconnected, and in some such embodiments, the sleeves are not interconnected. In some embodiments, each sleeve is adapted to receive only one medical line, and in some specific embodiments, each sleeve is adapted to receive only a particular type of medical line.

More generally, in the various embodiments, the protective sleeves may be provided in two or more or a range of pre-selected lengths to allow for accommodation of a range of standard medical line lengths.

Likewise, in the various embodiments, the protective sleeves may be formed in segments of pre-selected lengths, or have perforations such that a desired length comprising one or several segments can be selected to provide a protective sleeve of a desired length.

In use, the systems provided herein allow for the securement of medical lines so as to derive a variety of benefits. Most critically for patient safety, the systems and devices provide for the prevention of strangulation of a patient, particularly incapacitated patients, and especially pediatric patients. Whether in the hospital or home-care settings, because medical practitioners and caregivers cannot be present at all times to ensure patient safety, prevention of entanglement with medical lines can help to prevent severe harm or death.

Alternate and additional benefits of the systems include minimizing the exposure of medical lines to contaminants. Since many medical lines are in direct communication with tissues and organs of a patient, there is a risk that the lines will provide a means of communicating pathogens into the patient. And these lines are typically in use for a period of several hours and even several days. Thus, during the term of use, the lines may come in contact with people, medical equipment, the floor and other lines. Enclosure of the lines is a means to minimize contamination. In addition, coding of the lines using the systems provided herein helps to ensure that clinical staff do not confuse two lines, and inadvertently administer drugs, food and other agents in a fashion that would be detrimental to the patient. Accommodation of a single line in a coded protective sleeve, and custom access to a particular line as described herein further aids in minimizing confusion. In addition, selection of materials for forming the devices enhances identification, and also enhances protection from pathogens. Accordingly, the present invention anticipates the provision of sleeve systems comprising two or more sleeves in accordance with the present invention, wherein the sleeves are color-coded or otherwise marked or patterned so as to be distinguishable from one another within the system.

Referring to the Figures, FIG. 1 is a partial detailed plan view of the underside of a representative embodiment of the systems described herein, in accordance with one embodiment of the present invention, shown in a fully opened position. FIG. 1 shows protective sleeve 1 comprising transparent panel 2 and opaque panel 3. Opaque panel 3 and transparent panel 2 are joined by a seam 4 with optional stitching upon reinforcement 4 held in a closed, folded position along the longitudinal axis by a series of Velcro closures 5 in this case disposed along optional folded flap portion 3a, with corresponding Velcro closures 6 disposed along transparent panel 2. FIG. 1 also shows that the Velcro closures may be disposed on an optional flap 3a such that the closures are able to be joined while not being exposed by folding the optional flap inward along directional line A. FIG. 1 also shows a series of optional attachment means, such as a series of additional flaps 7 that may be used to attach to a support means near the patient and/or near the medical instruments or devices served by the medical lines. For instance, the flaps 7 that may be simple fabric flaps that may be tucked beneath a bed mattress holding the patient, or they may be provided with Velcro closures, button holes, loops or snaps (for corresponding buttons, hooks or snap fittings, respectively provided on an opposing surface) such that the flaps 7 may be used as a supplemental closure of the sleeve, in this case wrapping around the folded panels 2 and 3 to be releasably attached thereto, such as on surface 3b. Optionally, the flaps may be provided with Velcro to be able to wrap around bed rails or I.V. poles. Other temporary fixtures, such as buttons, snaps or hooks may be used for this same purpose, depending upon the support to which the protective sleeve is to be temporarily attached.

The transparent panel 2 preferably will be constructed of an application-appropriate transparent plastic material that is flexible enough to accommodate the shapes, position and flexion of the contained medical lines in accordance with their movement during positioning and operation.

The opaque panel 3 preferably may be constructed of an opaque material, such as cloth or plastic, again having a similar functional flexibility profile, and preferably being adapted to contain or support the rigid reinforcement members 8. The opaque panel 3 preferably may be constructed of a bi-layer, so as to allow the inclusion of rigid reinforcement members 8 held in position, such as through stitching 9 or equivalent means, such as adhesives or other mechanical means. See FIGS. 2 and 4.

Figure 2:
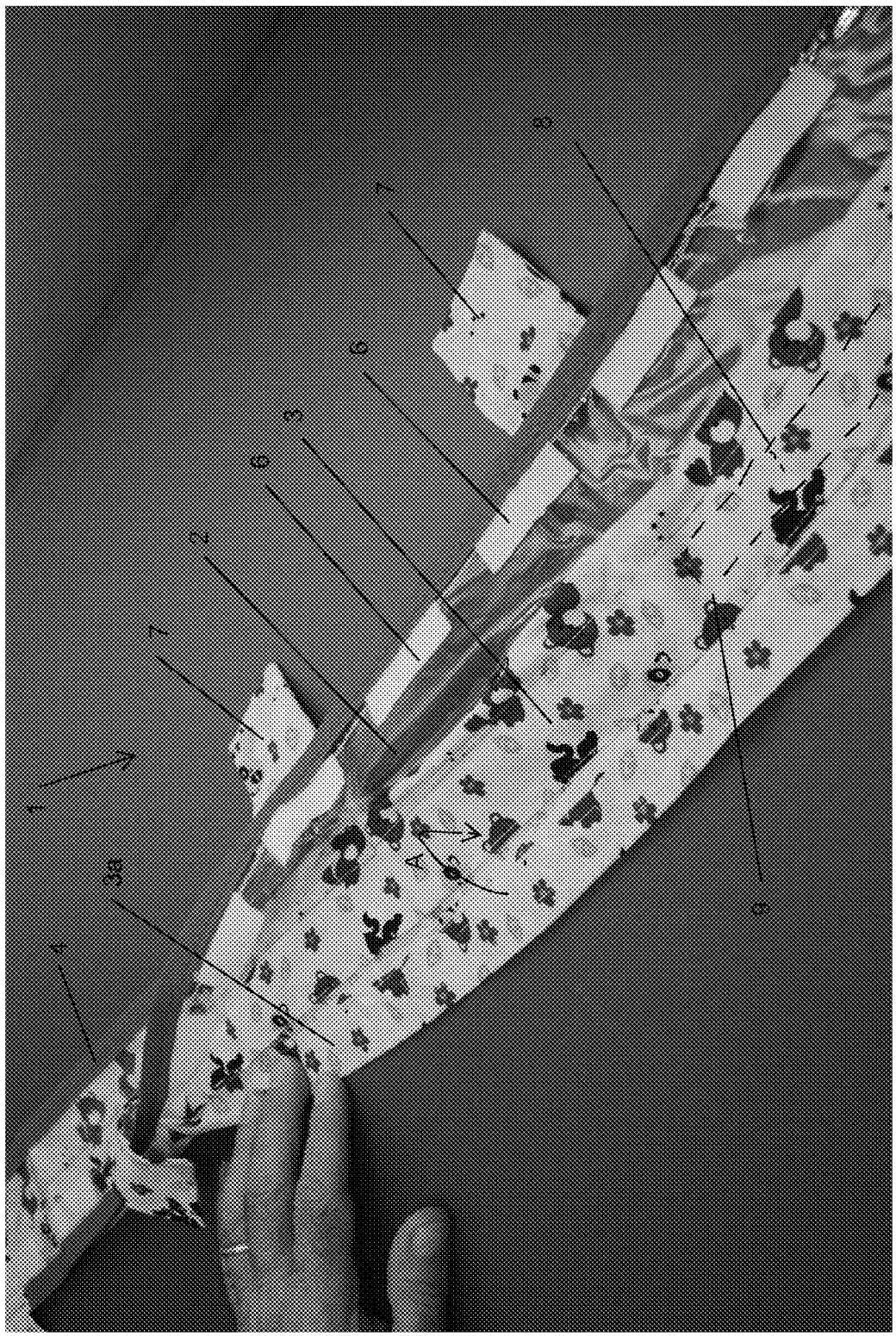
FIG. 2 is a perspective view of the top side of a representative embodiment of the systems described herein, in accordance with one embodiment of the present invention, shown in a partially opened position.

FIG. 2 is a perspective view of the top side of a representative embodiment of the systems described herein, in accordance with one embodiment of the present invention, shown in a partially opened position, wherein like reference numerals are used to indicate portions thereof. This view shows in greater detail the formation of the closed sleeve from the cooperating opaque panel 3 and transparent panel 2 that are joined by optional stitching upon reinforcement 4. This view also shows the Velcro closures 5 in this case disposed along optional folded flap portion 3a along direction line A, with corresponding Velcro closures 6 to capture them.

Figure 3:
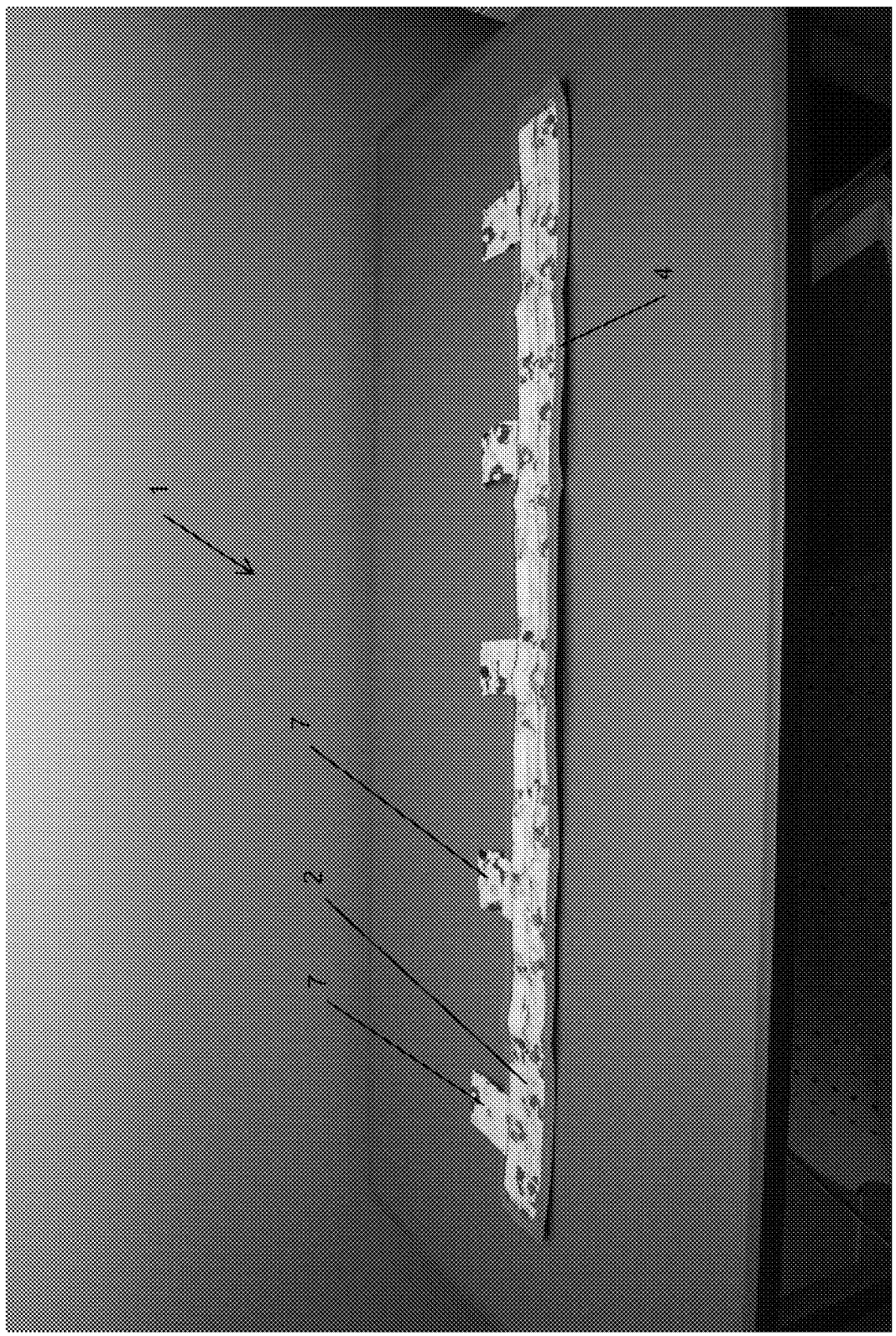
FIG. 3 is a perspective view of the top side of a representative embodiment of the systems described herein, in accordance with one embodiment of the present invention, shown in a fully closed position.

FIG. 3 is a perspective view of the top side of a representative embodiment of the systems described herein, in accordance with one embodiment of the present invention, shown in a fully closed position, wherein like reference numerals are used to indicate portions thereof.

Figure 4:
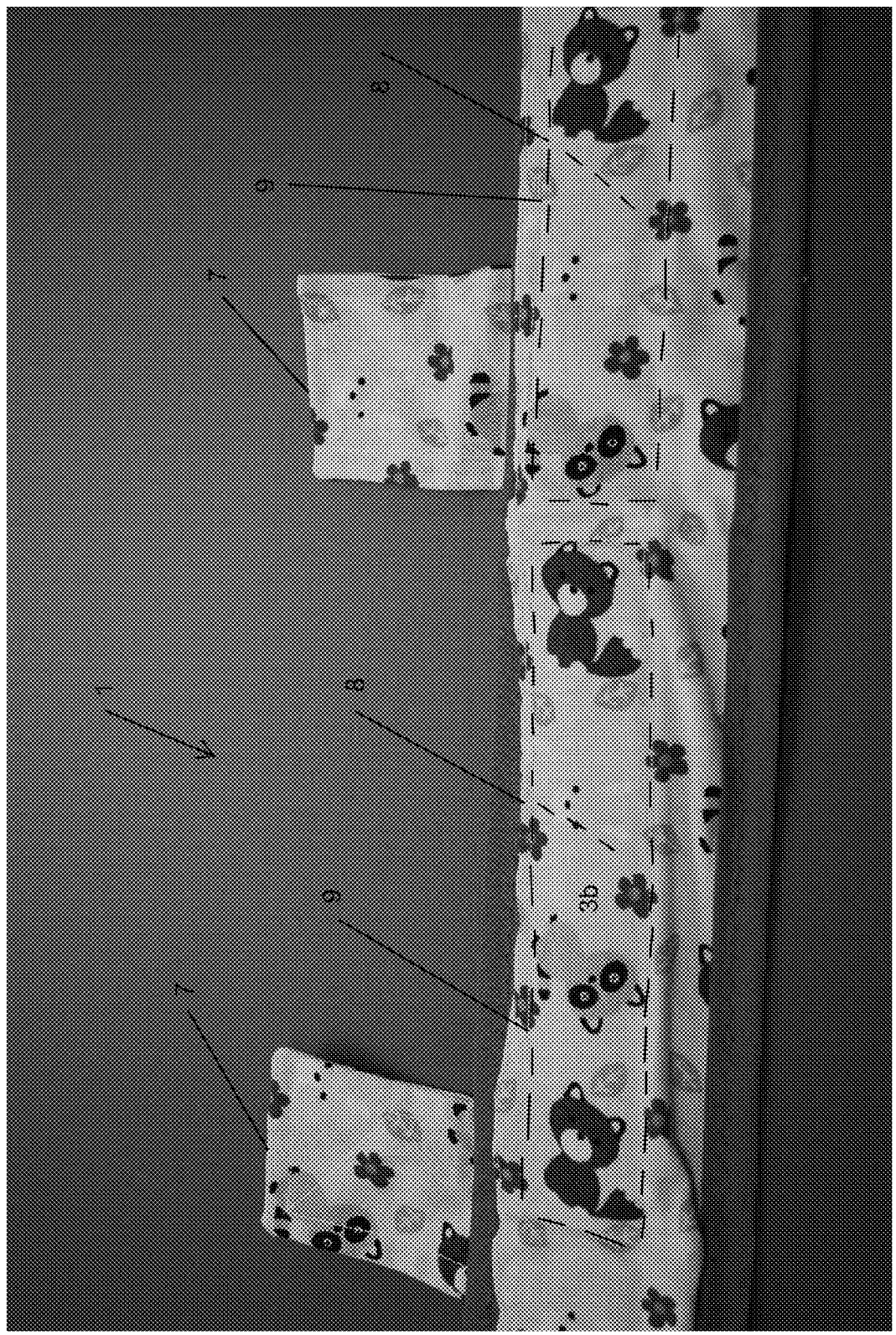
FIG. 4 is a detailed perspective view of the underside of a representative embodiment of the systems described herein, in accordance with one embodiment of the present invention, shown in a fully closed position.

FIG. 4 is a detailed perspective view of the underside of a representative embodiment of the systems described herein, in accordance with one embodiment of the present invention, shown in a fully closed position wherein like reference numerals are used to indicate portions thereof. This Figure shows the opaque panel 3 constructed as a bi-layer of material, so as to allow the inclusion of rigid reinforcement members 8 held in position, such as through stitching 9 or equivalent means, such as adhesives or other mechanical means. The rigid reinforcement members 8 may be of any length, though typically 2-12 inches for example, and may be made of any application-appropriate material, such as wood, plastic or metal. These members may be placed in accordance with the positions of optional perforations to allow the sleeve to be customized as to length, as described below. The rigid reinforcement members 8 may be in the form of incorporated sections of relatively thicker plastic in a plastic sleeve portion.

Figure 5:
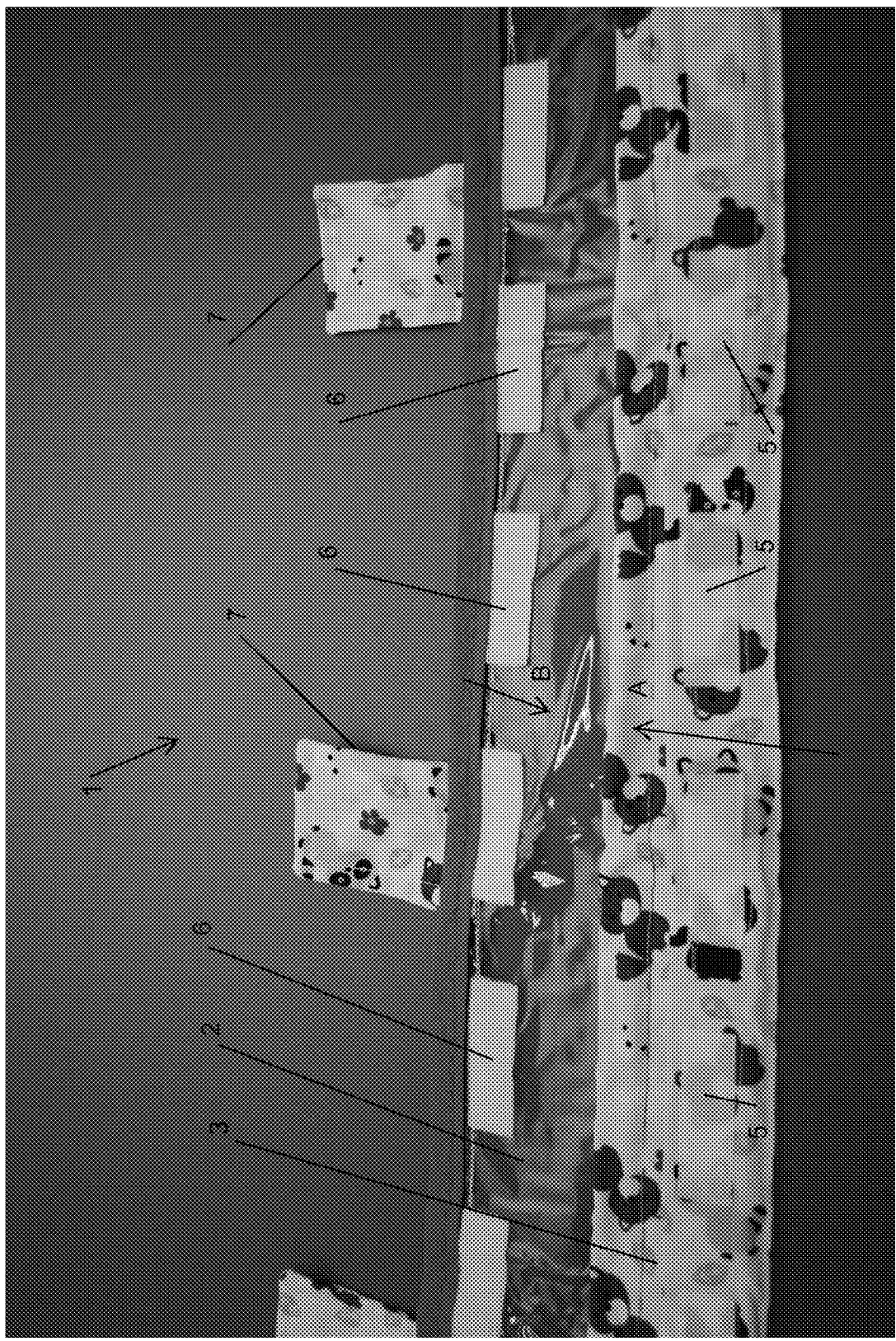
FIG. 5 is a detailed plan view of the top side of a representative embodiment of the systems described herein, in accordance with one embodiment of the present invention, shown in a fully opened position, as shown in FIG. 1.

FIG. 5 is a detailed plan view of the top side of a representative embodiment of the systems described herein, in accordance with one embodiment of the present invention, shown in a fully opened position, as shown in FIG. 1 wherein like reference numerals are used to indicate portions thereof. This view shows in more detail how optional flap 3a closes so as to able to be joined while not being exposed by optional flap 3a, having been folded inward along directional line A, after which the transparent panel is closed thereupon along directional line B, such Velcro closures 5 capture Velcro closures 6.

Figure 6:
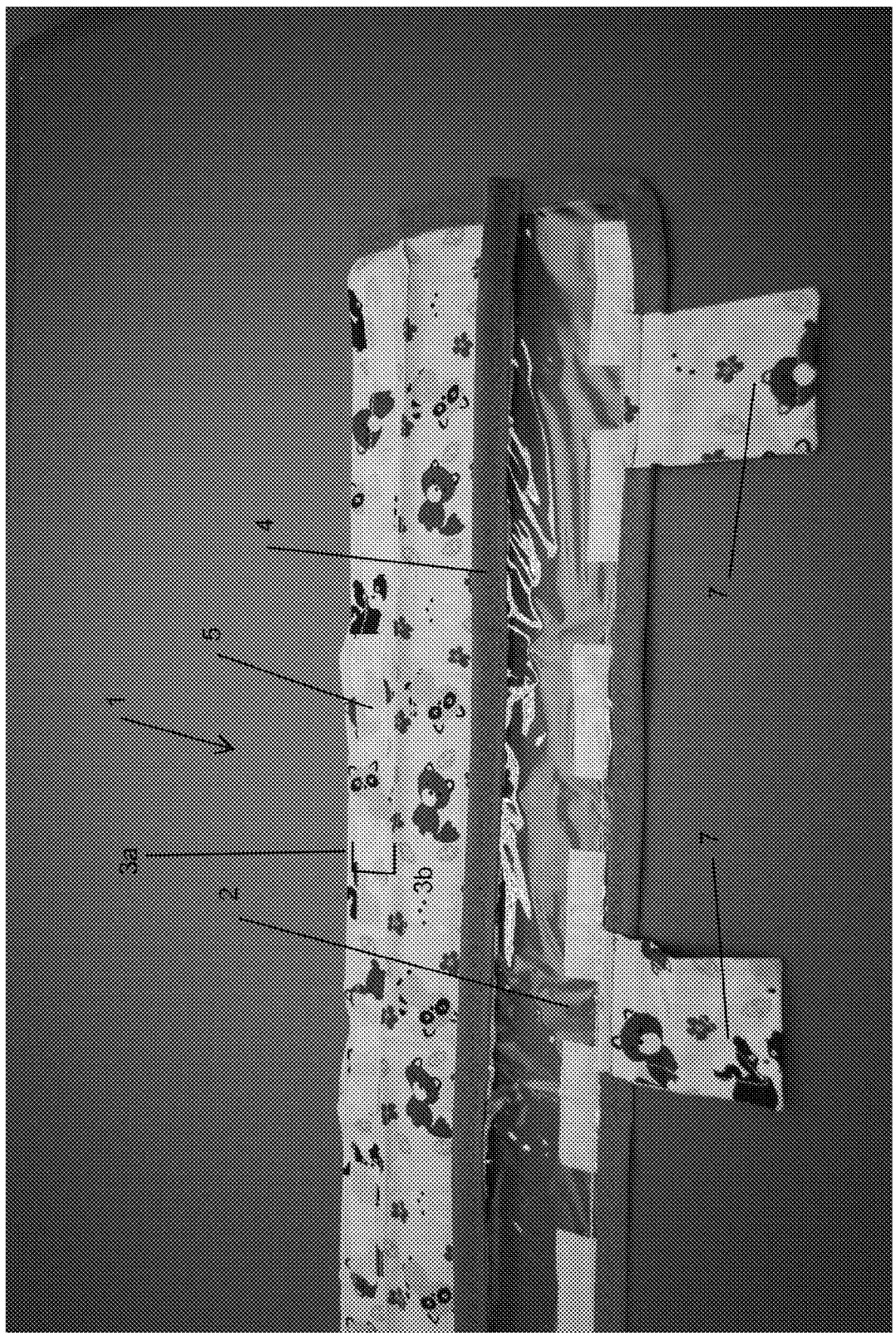
FIG. 6 is a partial detailed plan view of one end of the underside of a representative embodiment of the systems described herein, in accordance with one embodiment of the present invention, shown in a fully open position.

FIG. 6 is a partial detailed plan view of one end of the underside of a representative embodiment of the systems described herein, in accordance with one embodiment of the present invention, shown in a fully opened position wherein like reference numerals are used to indicate portions thereof.

FIG. 7 is a detailed plan view of the underside of a representative embodiment of the systems described herein, in accordance with one embodiment of the present invention, shown in a fully opened position wherein like reference numerals are used to indicate portions thereof.

FIG. 8 is a detailed plan view of the top side of a representative embodiment of the systems described herein, in accordance with one embodiment of the present invention, shown in a fully opened position, as shown in FIG. 1, wherein like reference numerals are used to indicate portions thereof.

Figure 9:
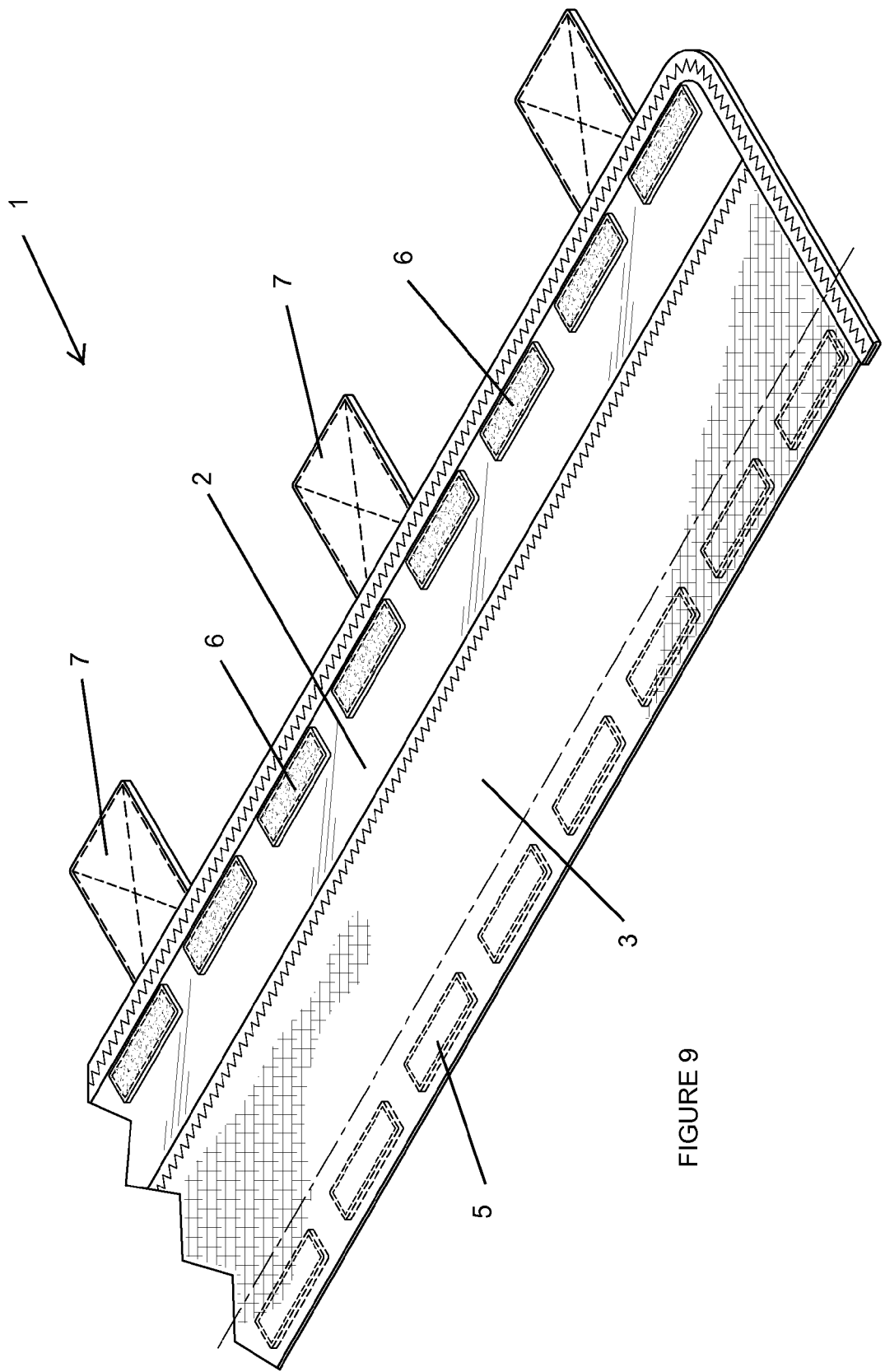
FIG. 9 is a detailed perspective view of the top side of a representative embodiment of the systems described herein, in accordance with one embodiment of the present invention, shown in a fully opened position, as shown in FIGS. 1 and 8.

FIG. 9 is a detailed perspective view of the top side of a representative embodiment of the systems described herein, in accordance with one embodiment of the present invention, shown in a fully opened position, as shown in FIGS. 1 and 8, wherein like reference numerals are used to indicate portions thereof.

Figure 9A:
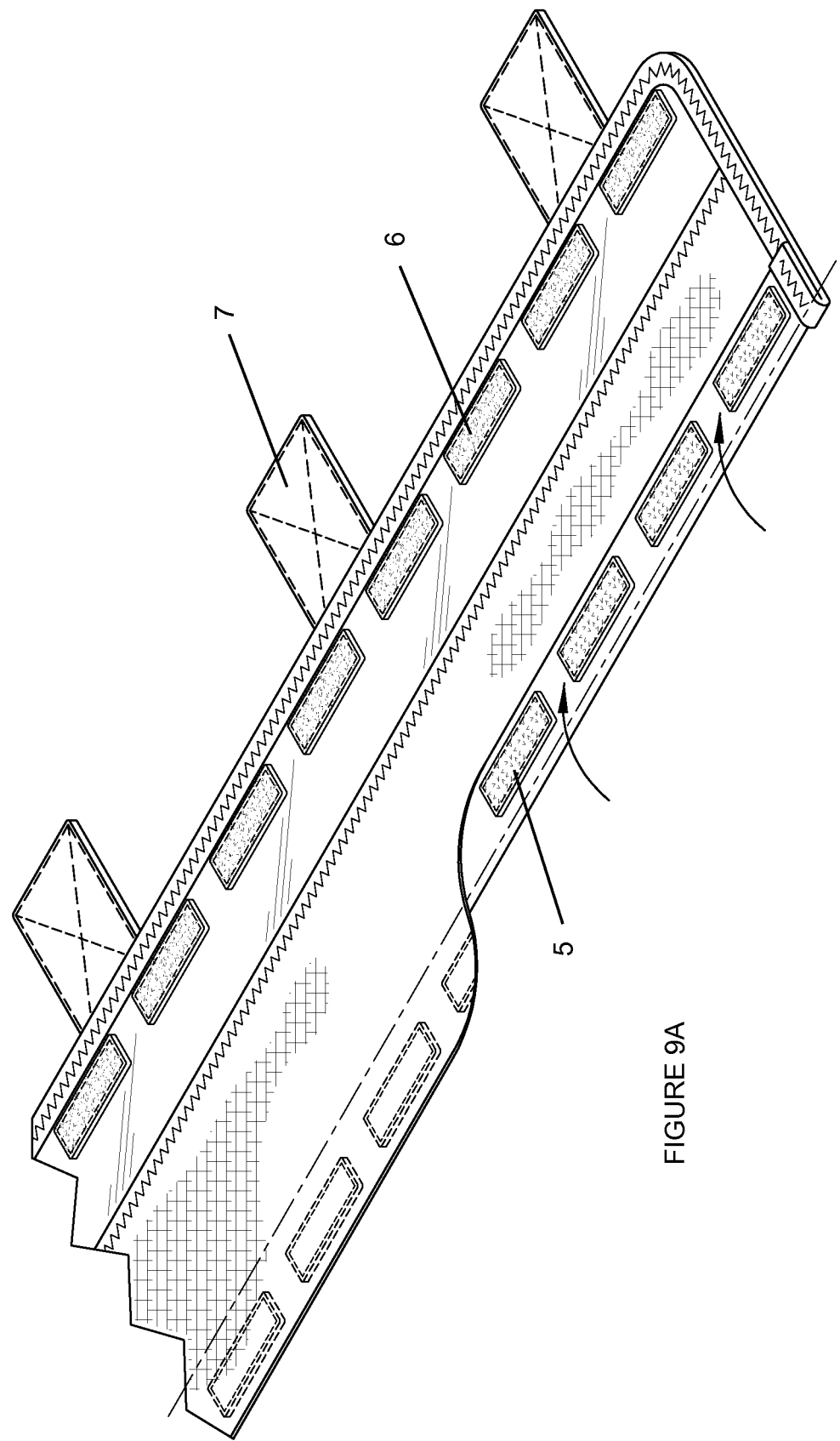
FIG. 9A is a detailed perspective view of the top side of a representative embodiment of the systems described herein, in accordance with one embodiment of the present invention, shown in a fully opened position, as shown in FIGS. 1 and 8.

FIG. 9A is a detailed perspective view of the top side of a representative embodiment of the systems described herein, in accordance with one embodiment of the present invention, shown in a fully opened position, as shown in FIGS. 1 and 8, wherein like reference numerals are used to indicate portions thereof.

Figure 9B:
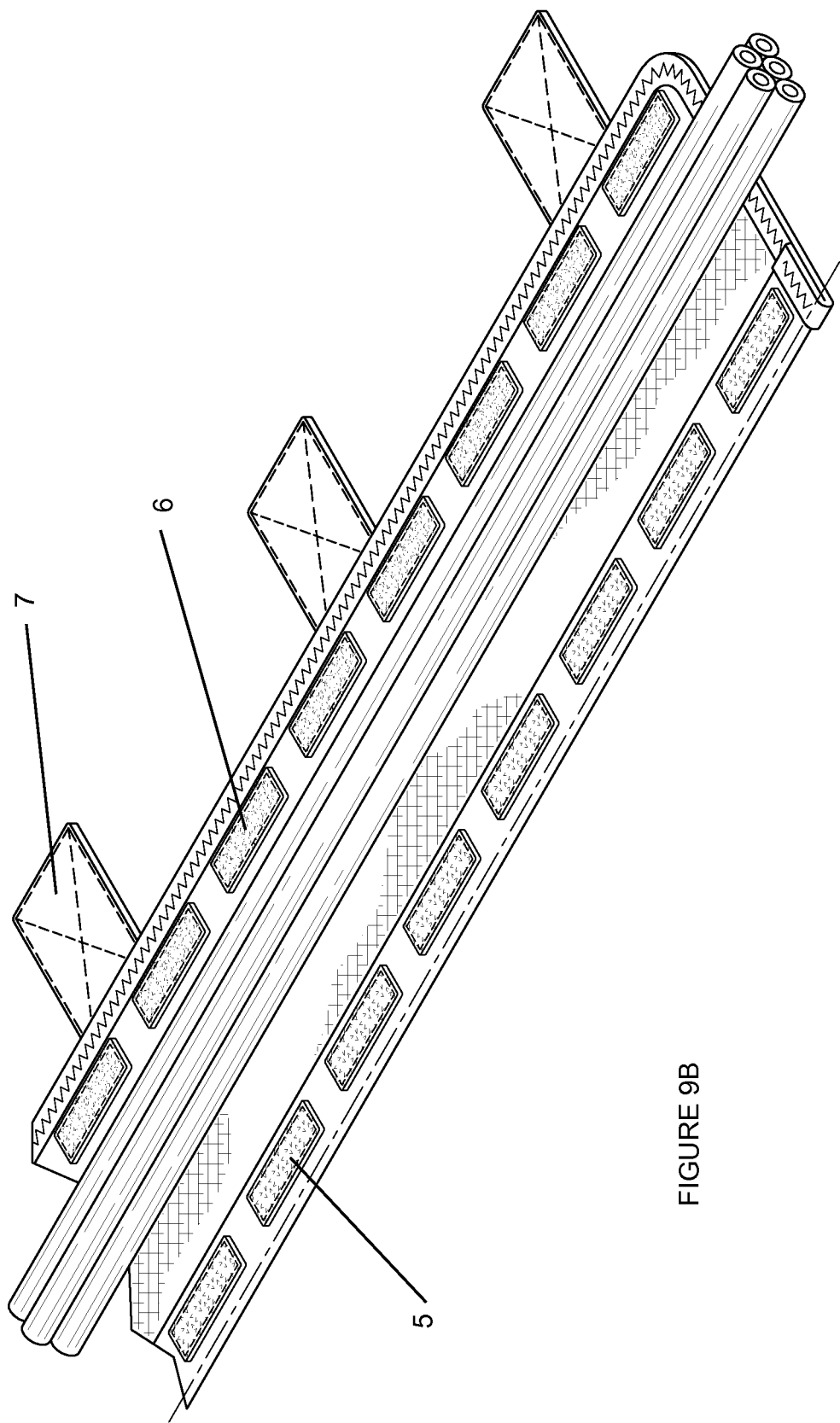
FIG. 9B is a detailed perspective view of the top side of a representative embodiment of the systems described herein, in accordance with one embodiment of the present invention, shown in a fully opened position, as shown in FIGS. 1 and 8.

FIG. 9B is a detailed perspective view of the top side of a representative embodiment of the systems described herein, in accordance with one embodiment of the present invention, shown in a fully opened position, as shown in FIGS. 1 and 8, wherein like reference numerals are used to indicate portions thereof.

Figure 9C:
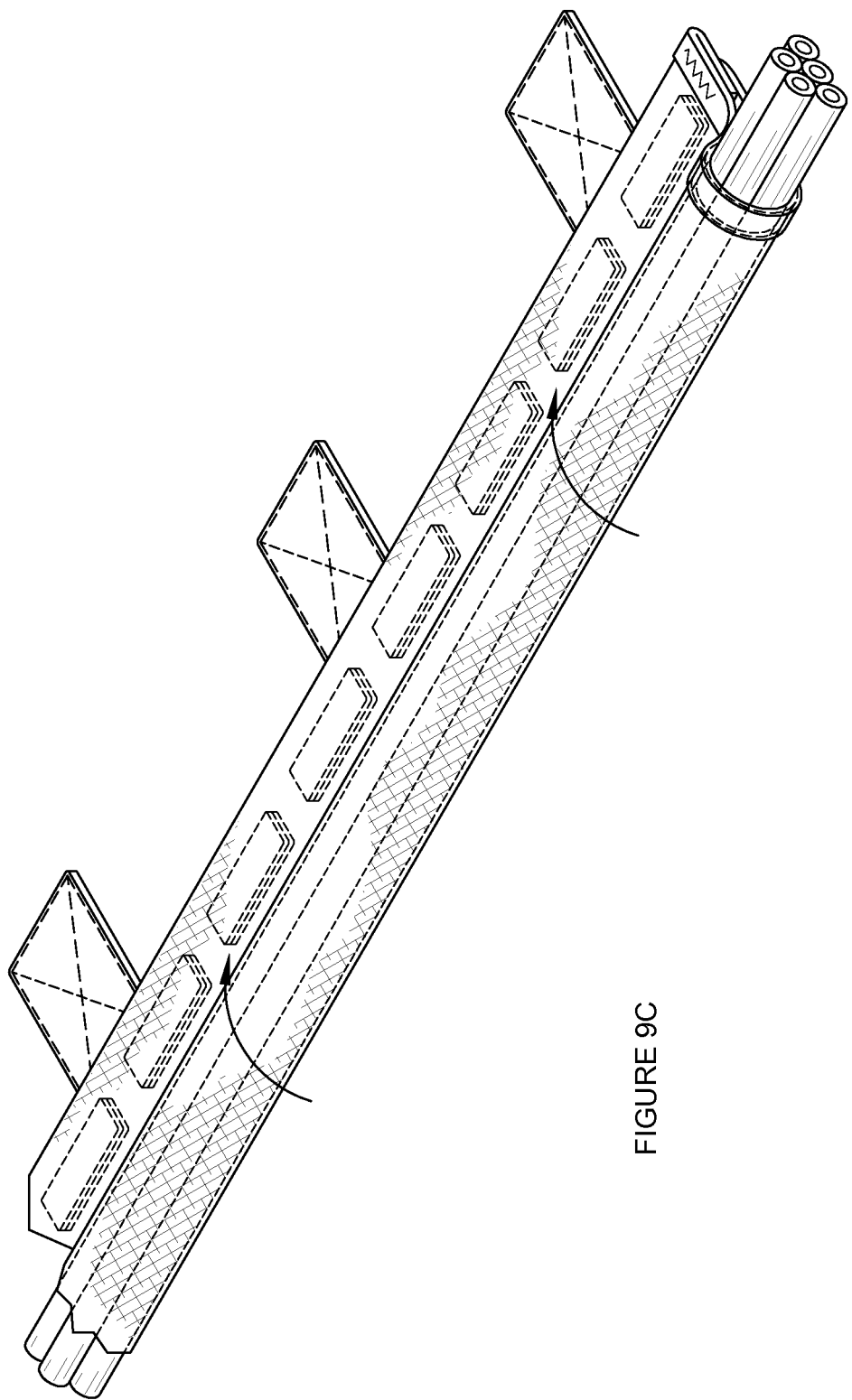
FIG. 9C is a detailed perspective view of the bottom side of a representative embodiment of the systems described herein, in accordance with one embodiment of the present invention, shown in a fully closed position.

FIG. 9C is a detailed perspective view of the bottom side of a representative embodiment of the systems described herein, in accordance with one embodiment of the present invention, shown in a fully closed position, wherein like reference numerals are used to indicate portions thereof.

Figure 10:
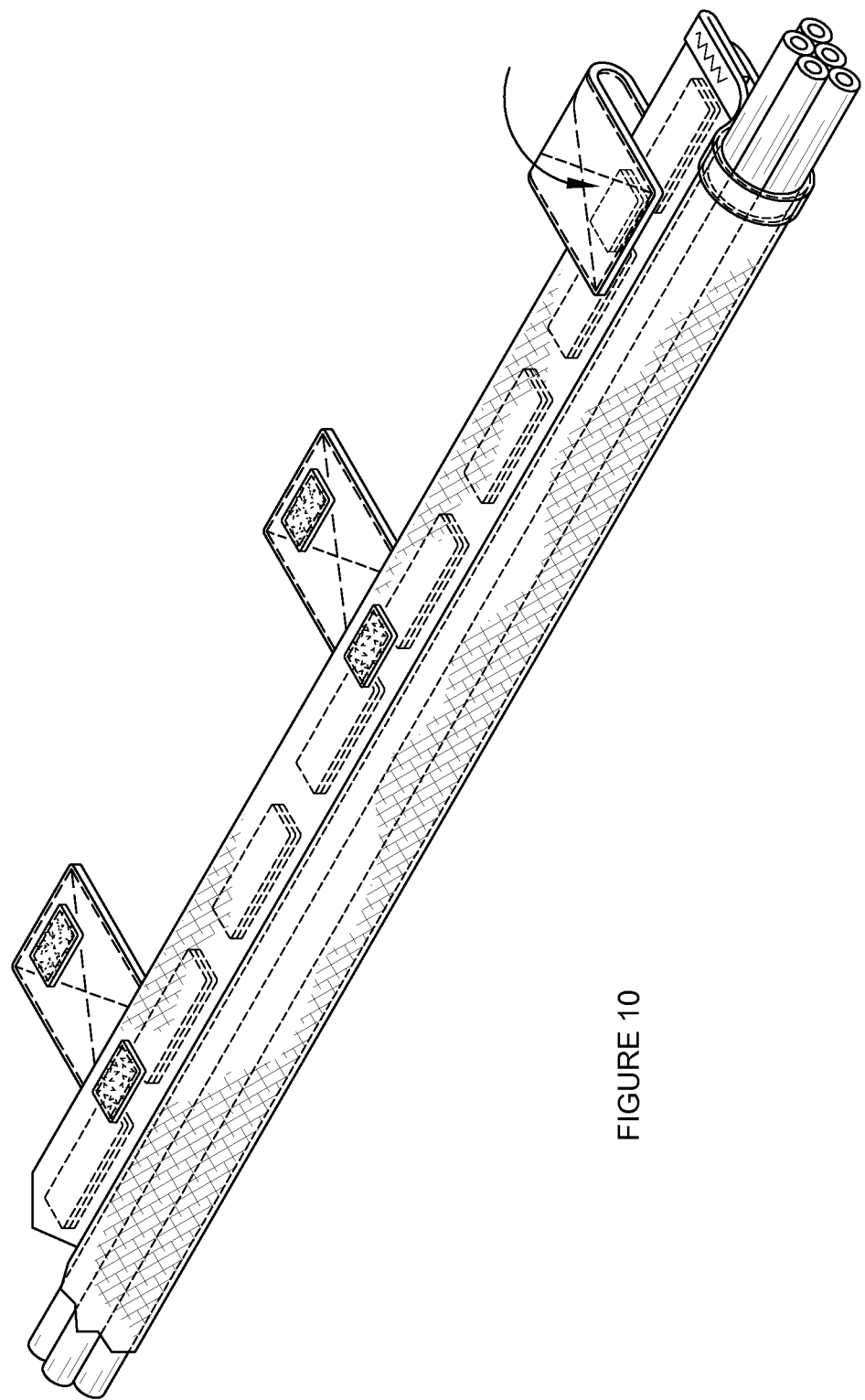
FIG. 10 is a detailed perspective view of the bottom side of a representative embodiment of the systems described herein, in accordance with one embodiment of the present invention, shown in a fully closed position.

FIG. 10 is a detailed perspective view of the bottom side of a representative embodiment of the systems described herein, in accordance with one embodiment of the present invention, shown in a fully closed position, wherein like reference numerals are used to indicate portions thereof.

As may be appreciated, the present invention may be constructed wholly of disposable materials, such as plastic, and, in this particular embodiment, the panels of sleeve 1 may be provided with a series of perforations to allow the length of the sleeve to be customized to a particular physical application.

The sleeve 1 may be provided with indicia or a pattern such that the sleeves may be used with a system to distinguish on set of medical lines (i.e., whether gas and/or fluid, electrically conductive or signal-transmissive, or combination thereof) from another set.

These Figures show how the protective sleeve of the present invention may be opened and closed about medical lines through the use of the releasable closures and optional reinforcements and supports, to keep them organized and free from tangling and the associated confusion.

The present invention also includes a method of protecting and/or organizing medical lines in one or more series, using the sleeve(s) of the present invention as described.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, any numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Other embodiments of the invention will be apparent to those skilled in the art from consideration of the specification and practice of the invention disclosed herein. It is intended that the specification and examples be considered as exemplary only, and that modifications may be made to the described embodiments without departing from the spirit and scope of the invention as defined in the claims.

What is claimed is:

1. A protective sleeve for containing medical lines extending along its longitudinal axis, said sleeve comprising:
   (a) a foldable sleeve comprising first and second side panels having a longitudinal axis, and adapted to be reversibly opened and closed along said longitudinal axis so as to form a conduit for medical lines, at least one of said panels being flexible and transparent, said foldable sleeve having a plurality of releasable closures to maintain said foldable sleeve in a folded closed position, and so as to permit said sleeve to be opened at different positions along its length; and
   (b) a plurality of elongate rigid members incorporated within at least one of said panels and aligned in a series along said longitudinal axis.

2. A protective sleeve according to claim 1 wherein said releasable closures are selected from the group consisting of hook-and-loop closures, magnets, hooks, buckles, buttons, zippers and snaps.

3. A protective sleeve according to claim 1, said releasable closures comprising a series of hook-and-loop closures disposed along a length of said protective sleeve so as to permit partial opening of said protective sleeve.

4. A protective sleeve according to claim 1, additionally comprising a supplementary attachment means for attaching said first and second side panels.

5. A protective sleeve according to claim 4, wherein said supplementary attachment means comprises a flap permanently attached to one of said first and second side panels, and adapted to be releasably attached to the other of said first and second side panels.

6. A protective sleeve according to claim 1 wherein said plurality of rigid members are enclosed within one of said panels.

7. A protective sleeve according to claim 6 wherein said plurality of rigid members are substantially the same length, and disposed in a series with flexible portions of said panels disposed therebetween, so as to permit said protective sleeve to be folded in a series of sections approximating the length of said rigid members.

8. A protective sleeve according to claim 1, additionally comprising an attachment means for attaching said protective sleeve to a stationary object.

9. A protective sleeve according to claim 8 wherein said attachment means for attaching said protective sleeve to said stationary object comprises a series of tabs disposed along a length of said protective sleeve and extending therefrom.

10. A protective sleeve according to claim 9 wherein said attachment means for attaching said protective sleeve to said stationary object comprises a series of tabs, releasably attached to said sleeve and disposed along a length of said protective sleeve and extending therefrom.

11. A protective sleeve according to claim 1, said sleeve containing a series of transverse perforations so as to be divisible into more than one portion.

12. A protective sleeve according to claim 1, said sleeve containing at least one medical line selected from the group consisting of intravenous lines used for the delivery of fluids, blood, and therapeutic and prophylactic agents, device monitoring lines, feeding tubes, and tubes for delivery of gas.

13. A protective sleeve according to claim 1 wherein said plurality of rigid members are disposed in a series with flexible portions of said panels disposed therebetween.

14. A protective sleeve according to claim 1 wherein said plurality of rigid members are enclosed within only one of said panels.

15. A protective sleeve for containing medical lines extending along its longitudinal axis, said sleeve comprising:
  (a) a foldable sleeve having a longitudinal axis and comprising first and second side panels, and adapted to be reversibly opened and closed along said longitudinal axis so as to form a conduit for medical lines, said first panel being flexible and transparent and said second panel being opaque, said foldable sleeve having a plurality of releasable closures to maintain said foldable sleeve in a folded closed position, and so as to permit said sleeve to be opened at different positions along its length, said releasable closures comprising a series of hook-and-loop closures disposed along a length of said protective sleeve so as to permit partial opening of said protective sleeve;
  (b) a plurality of elongate rigid members incorporated within said second panel and aligned in a series along said longitudinal axis; and
  (c) attachment means for attaching said protective sleeve to a stationary object.

16. A protective sleeve according to claim 15 wherein said attachment means for attaching said protective sleeve to said stationary object comprises a series of tabs disposed along a length of said protective sleeve and extending therefrom.

17. A protective sleeve according to claim 15, said sleeve containing a series of transverse perforations so as to be divisible into more than one portion.

18. A protective sleeve according to claim 17, said sleeve containing at least one medical line selected from the group consisting of intravenous lines used for the delivery of fluids, blood, and therapeutic and prophylactic agents, device monitoring lines, feeding tubes, and tubes for delivery of gas.

19. A protective sleeve for containing medical lines extending along its longitudinal axis, said sleeve comprising:
  (a) a foldable sleeve having a longitudinal axis and comprising first and second side panels, and adapted to be reversibly opened and closed along said longitudinal axis so as to form a conduit for medical lines, said first panel being flexible and transparent and said second panel being opaque, said foldable sleeve having a plurality of releasable closures to maintain said foldable sleeve in a folded closed position, and so as to permit said sleeve to be opened at different positions along its length, said releasable closures comprising a series of hook-and-loop closures disposed along a length of said protective sleeve so as to permit partial opening of said protective sleeve;
  (b) a plurality of elongate rigid members incorporated within said second panel and aligned along said longitudinal axis, wherein said plurality of elongate rigid members are substantially the same length, and aligned in a series with flexible portions of said panels disposed therebetween, so as to permit said protective sleeve to be folded in a series of lengths approximating the length of said elongate rigid members; and
  (c) attachment means for attaching said protective sleeve to a stationary object.

20. A protective sleeve according to claim 19, said sleeve containing at least one medical line selected from the group consisting of intravenous lines used for the delivery of fluids, blood, and therapeutic and prophylactic agents, device monitoring lines, feeding tubes, and tubes for delivery of gas.

21. A protective sleeve for containing medical lines extending along its longitudinal axis, said sleeve comprising:
  (a) a foldable sleeve comprising first and second side panels having a longitudinal axis, and adapted to be reversibly opened and closed along said longitudinal axis so as to form a conduit for medical lines, at least one of said panels being flexible and transparent, said foldable sleeve having a plurality of releasable closures to maintain said foldable sleeve in a folded closed position, said releasable closures comprising a series of closures disposed along a length of said protective sleeve so as to permit partial opening of said protective sleeve and to permit said sleeve to be opened at different positions along its length; and
  (b) a plurality of elongate rigid members incorporated within at least one of said panels and aligned in a series along said longitudinal axis.

22. A protective sleeve for containing medical lines extending along its longitudinal axis, said sleeve comprising:
  (a) a foldable sleeve comprising first and second side panels having a longitudinal axis, and adapted to be reversibly opened and closed along said longitudinal axis so as to form a conduit for medical lines, at least one of said panels being flexible and transparent, said foldable sleeve having a plurality of releasable closures comprising a series of hook-and-loop closures disposed along a length of said sleeve to maintain said foldable sleeve in a folded closed position, and so as to permit partial opening of said sleeve such that said sleeve may open at different positions along its length;
  (b) a plurality of elongate rigid members incorporated within at least one of said panels and aligned in a series along said longitudinal axis, wherein said plurality of rigid members are substantially the same length, enclosed within one of said panels, and disposed in a series with flexible portions of said panels disposed therebetween, so as to permit said protective sleeve to be folded in a series of sections approximating the length of said rigid members; and (c) supplementary attachment means for attaching said first and second side panels comprising a flap permanently attached to one of said first and second side panels, and adapted to be releasably attached to the other of said first and second side panels.

* * * * *